US012551374B2

(12) United States Patent
Kim et al.

(10) Patent No.: US 12,551,374 B2
(45) Date of Patent: Feb. 17, 2026

(54) PUNCHING-TYPE IRIDOTOMY INSTRUMENT

(71) Applicants: INDUSTRY-ACADEMIC COOPERATION FOUNDATION GYEONGSANG NATIONAL UNIVERSITY, Jinju-si (KR); KOREA UNIVERSITY RESEARCH AND BUSINESS FOUNDATION, Seoul (KR)

(72) Inventors: Seong Jae Kim, Jinju-si (KR); Youngsub Eom, Seoul (KR)

(73) Assignees: INDUSTRY-ACADEMIC COOPERATION FOUNDATION GYEONGSANG NATIONAL UNIVERSITY, Jinju-si (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 175 days.

(21) Appl. No.: 18/288,336

(22) PCT Filed: Apr. 29, 2022

(86) PCT No.: PCT/KR2022/006217
§ 371 (c)(1),
(2) Date: Oct. 25, 2023

(87) PCT Pub. No.: WO2022/231395
PCT Pub. Date: Nov. 3, 2022

(65) Prior Publication Data
US 2024/0238122 A1 Jul. 18, 2024

(30) Foreign Application Priority Data
Apr. 30, 2021 (KR) ........................ 10-2021-0056618

(51) Int. Cl.
*A61F 9/007* (2006.01)

(52) U.S. Cl.
CPC ...... *A61F 9/00763* (2013.01); *A61F 9/00781* (2013.01)

(58) Field of Classification Search
CPC .. A61F 9/00763; A61F 9/00781; A61F 9/007; A61B 17/2804; A61B 17/285; A61B 17/32053
See application file for complete search history.

(56) References Cited

U.S. PATENT DOCUMENTS 5,843,099 A * 12/1998 Nichols .............. A61B 17/0625 606/147
2012/0143222 A1* 6/2012 Dravis ............... A61B 17/0469 606/145
2014/0371790 A1* 12/2014 Hatch ................ A61B 17/0469 606/223

FOREIGN PATENT DOCUMENTS

CN 212996679 U 4/2021
JP 06-047048 A 2/1994
(Continued)

OTHER PUBLICATIONS

International Search Report of PCT/KR2022/006217 dated Aug. 18, 2022 [PCT/ISA/210].

*Primary Examiner* — Ashley L Fishback
*Assistant Examiner* — Chima U Igboko
(74) *Attorney, Agent, or Firm* — Sughrue Mion, PLLC

(57) ABSTRACT

Provided is a punching-type iridotomy instrument including a grip manipulation part configured to be manipulated to be opened or closed by a user while being held by the user's hand, an extension shaft extending from the grip manipulation part, and a punching operating unit extending from the extension shaft and configured to perform an operation of forming a hole in a predetermined site of a peripheral portion
(Continued)

of an iris in conjunction with an operation of the grip manipulation part performed by the user's manipulation, in which the grip manipulation part includes a first round shaft, a second round shaft, a spring disposed between the first and second round shafts and configured to exert elasticity for pushing the second round shaft, and a wire configured to connect the second round shaft and the punching operating unit.

6 Claims, 12 Drawing Sheets

(56) References Cited

FOREIGN PATENT DOCUMENTS

| | | | |
|---|---|---|---|
| JP | 2007-000944 | A | 1/2007 |
| KR | 10-2010-0096050 | A | 9/2010 |
| KR | 10-2019-0024157 | A | 3/2019 |

* cited by examiner

【FIG 1】
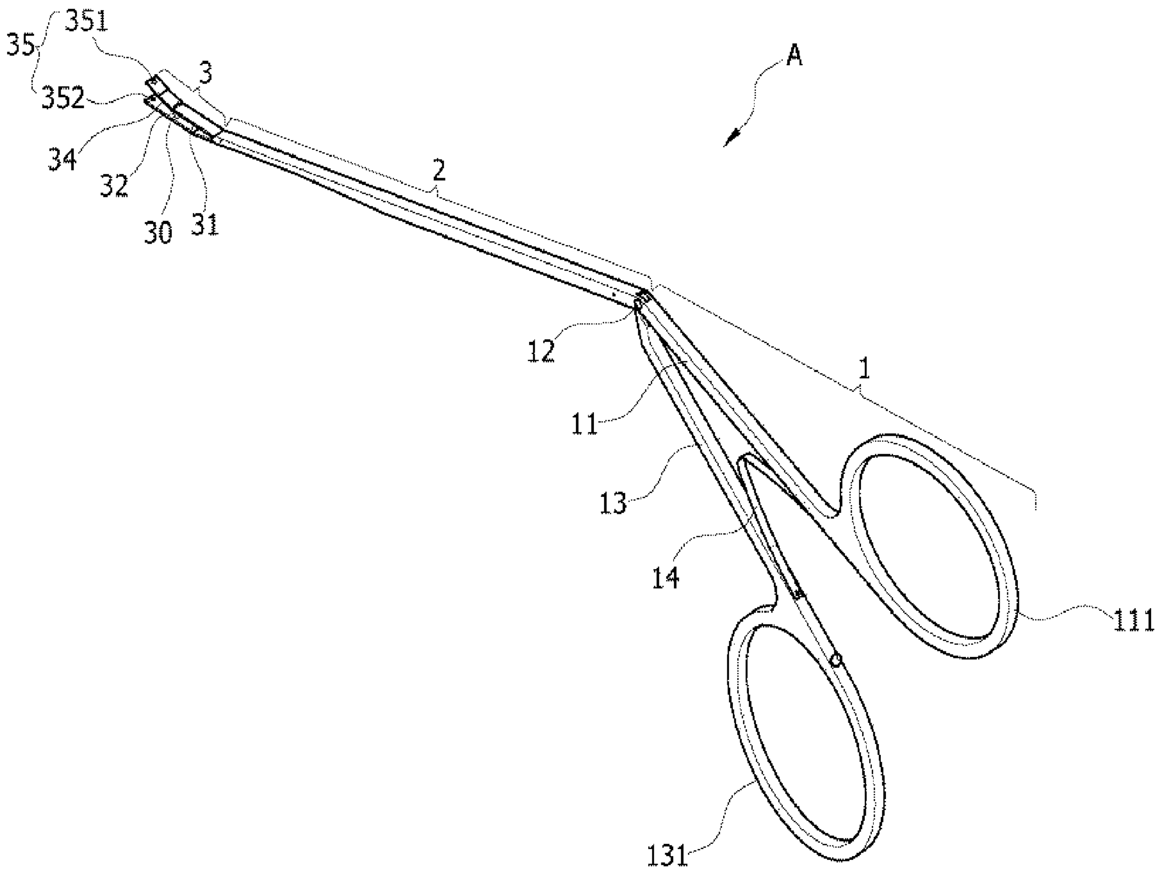

[FIG. 2]
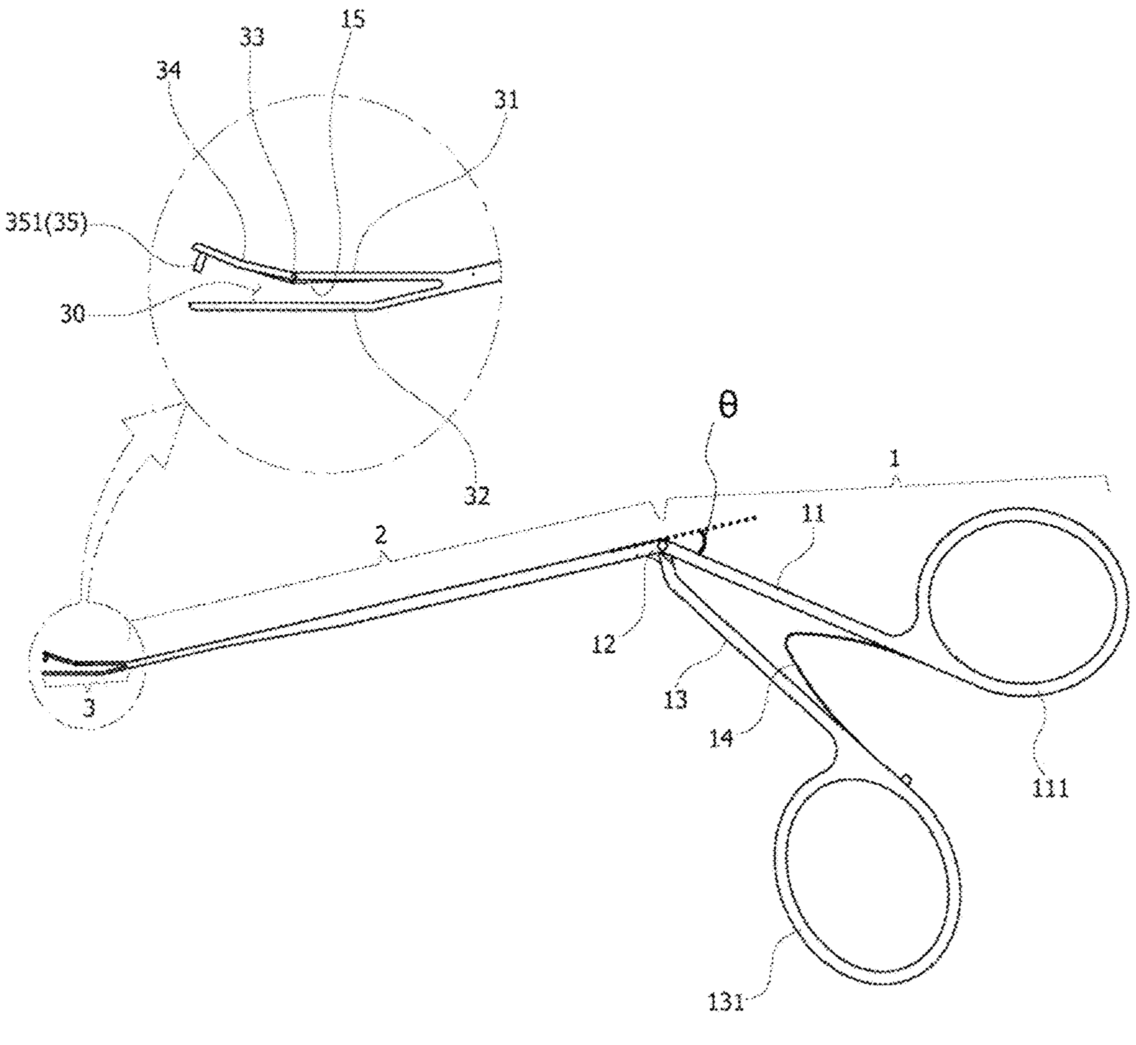

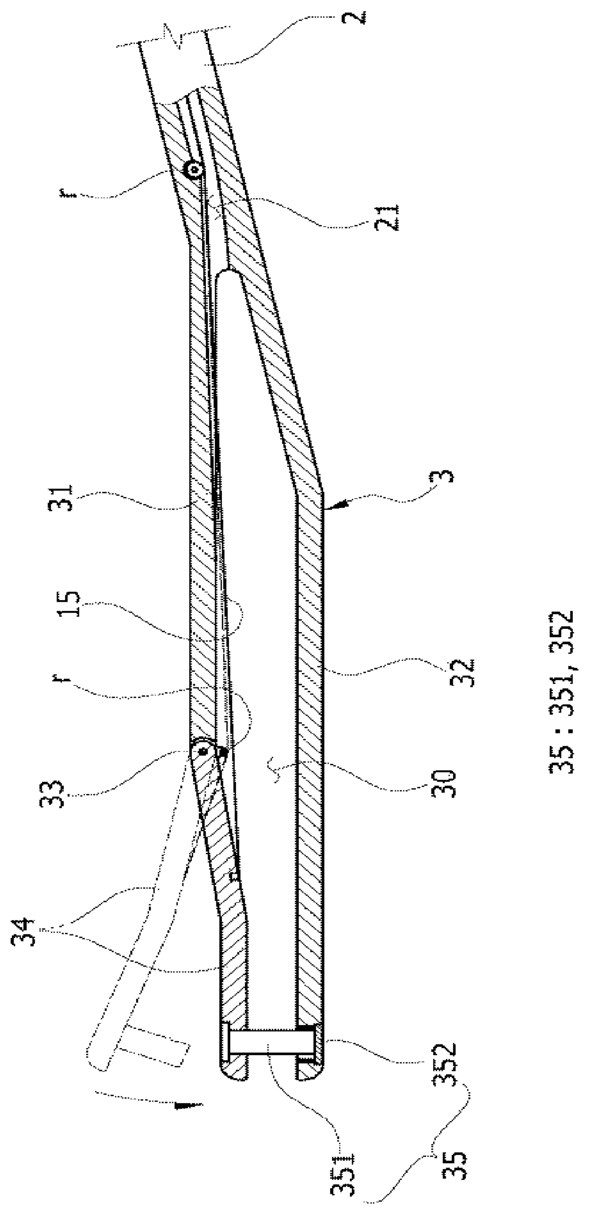
【FIG 3】

【FIG 4】
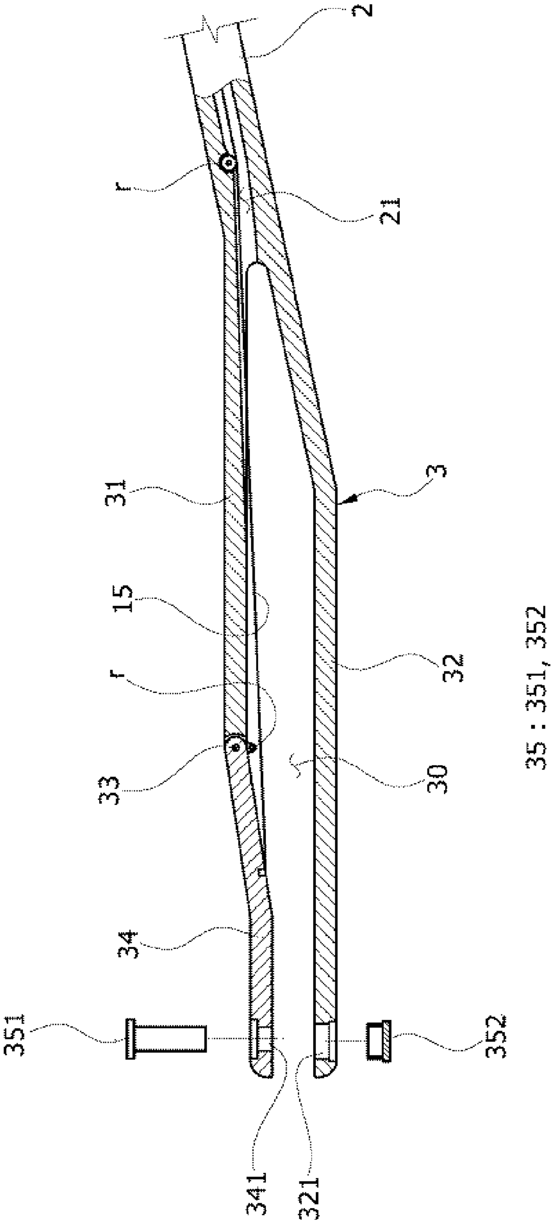

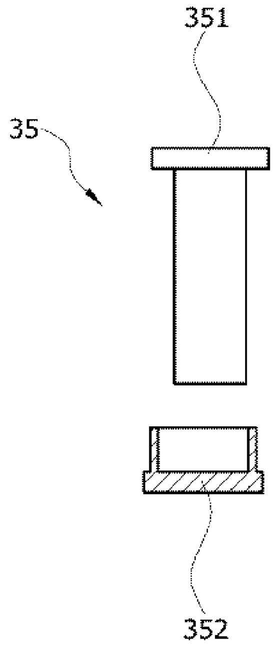
[ FIG 5A]
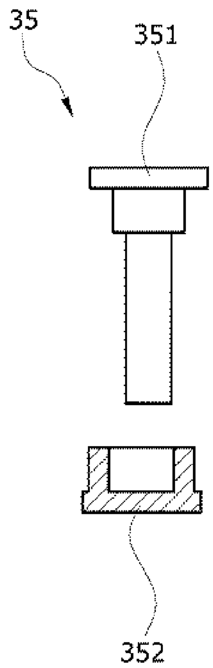
[ FIG 5B]
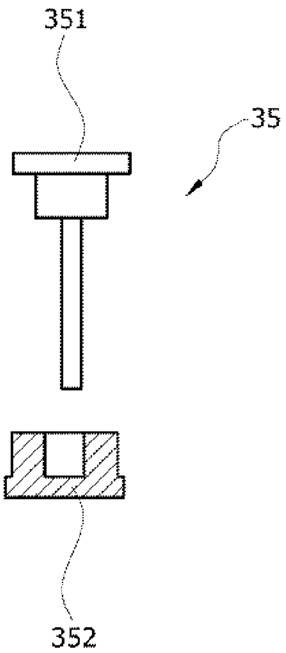
[ FIG 5C]

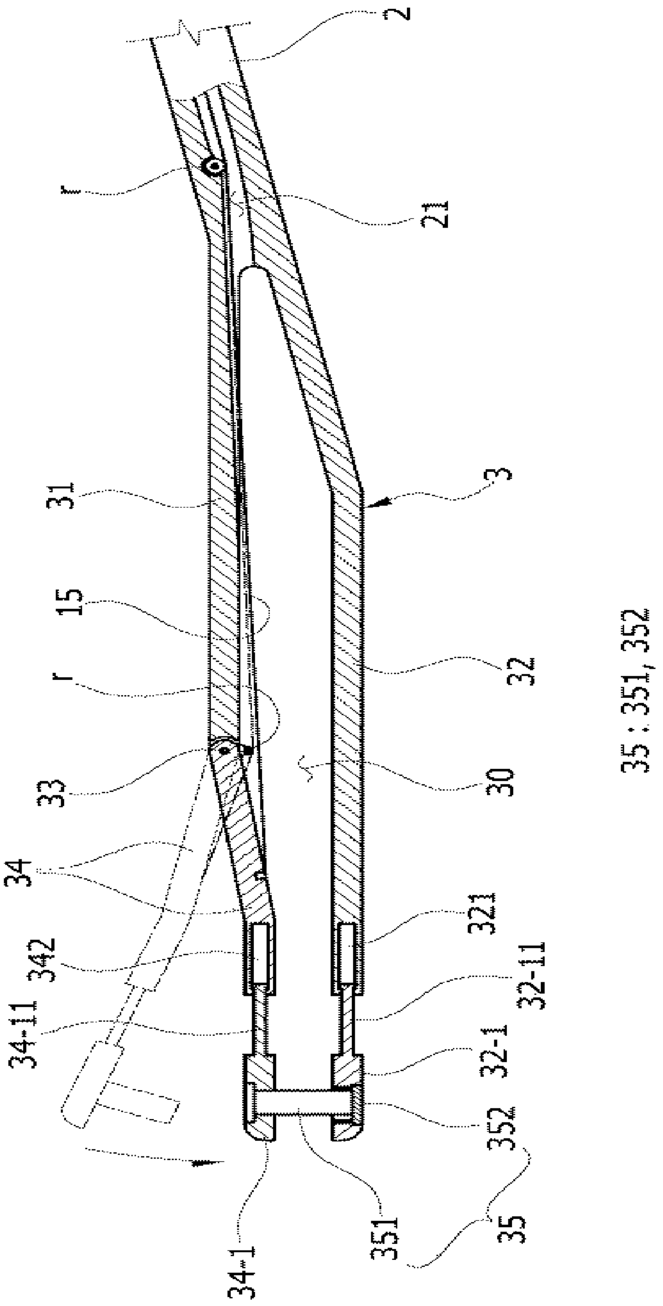
【FIG 6】

【 FIG 7A】
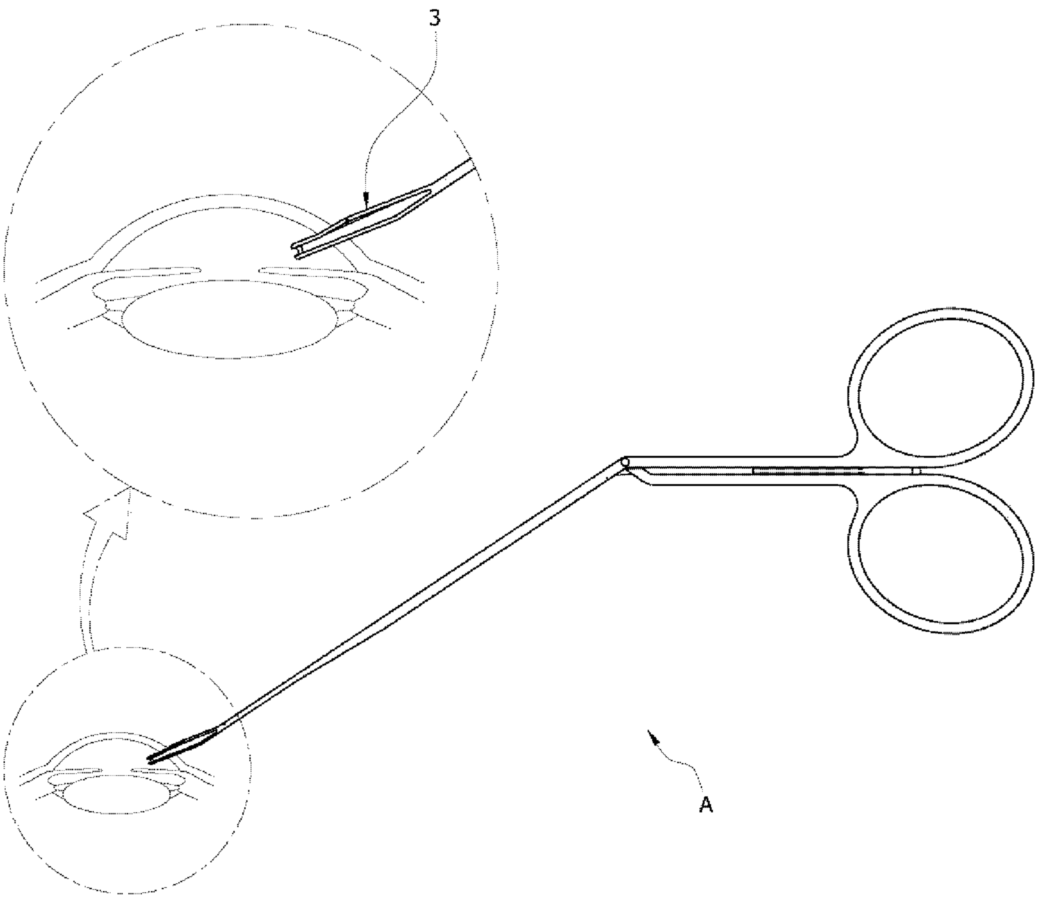

【 FIG 7B】
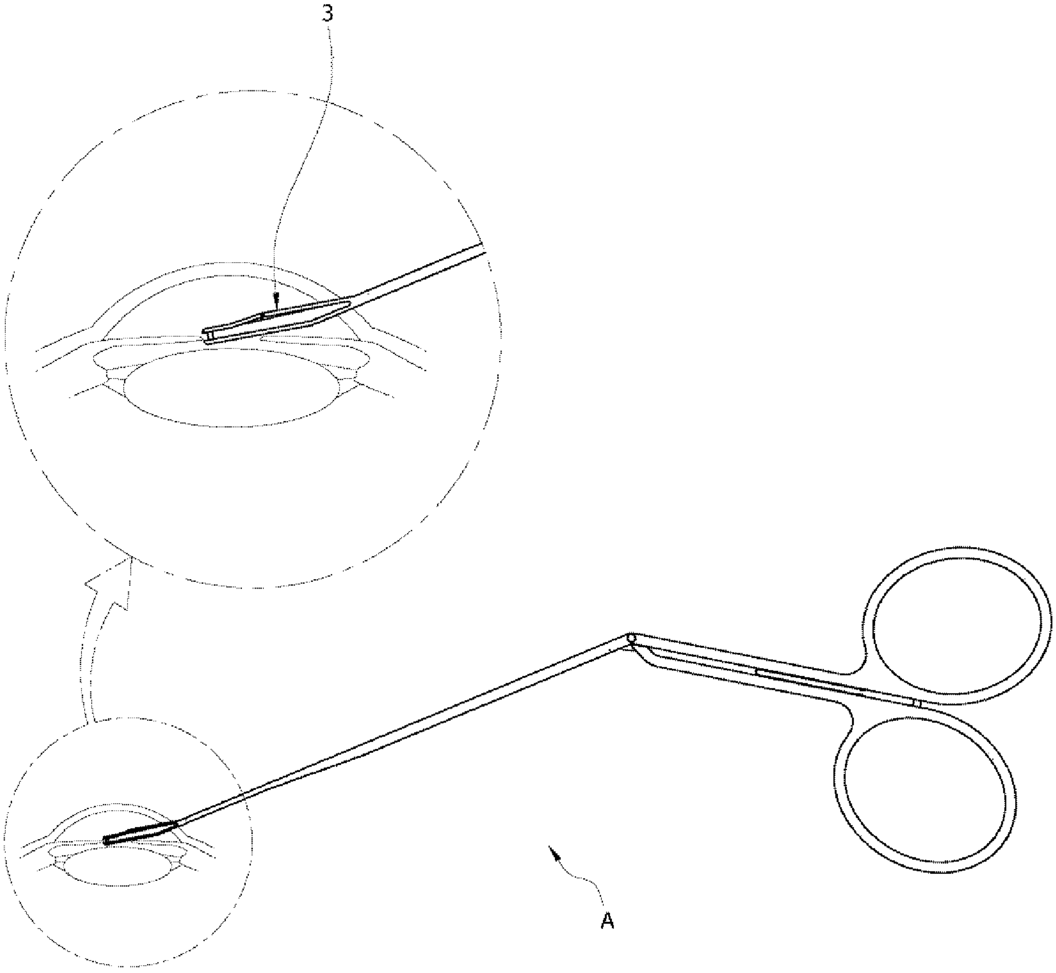

【 FIG 7C】
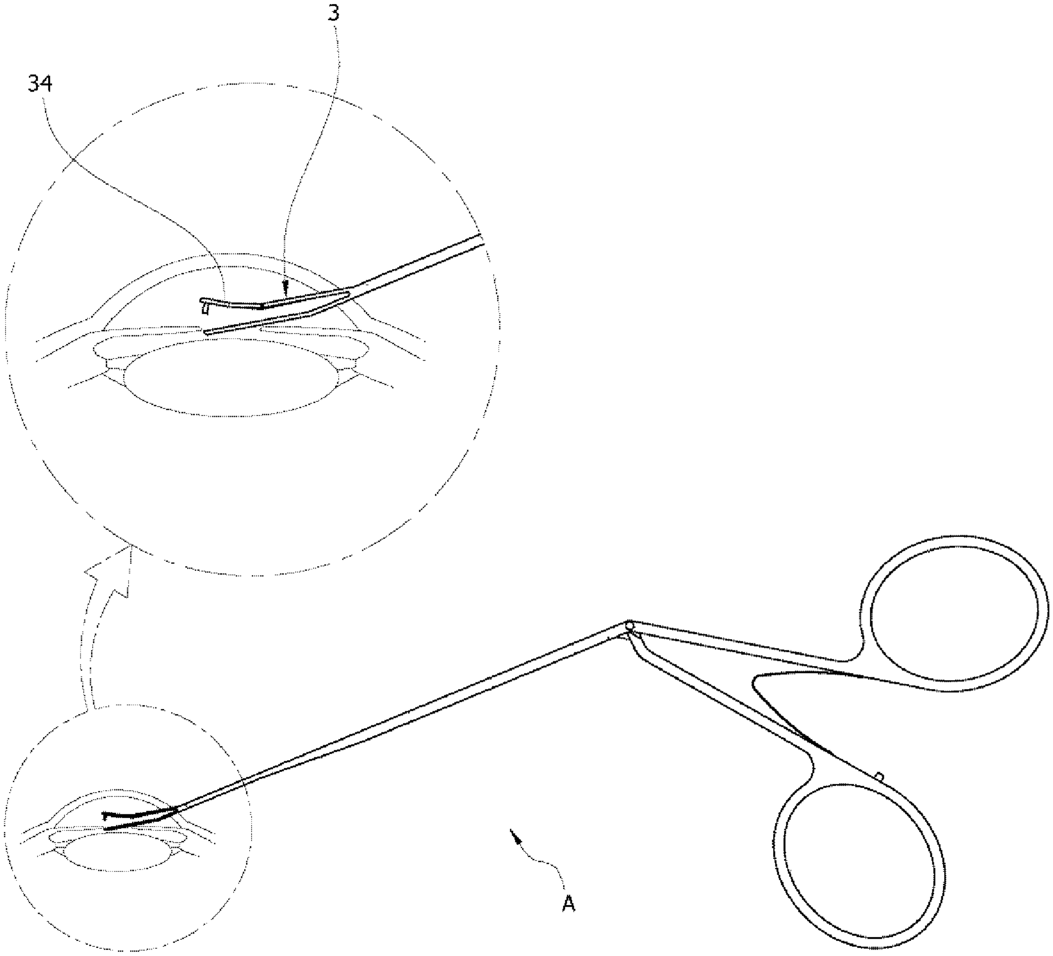

【 FIG 7D】
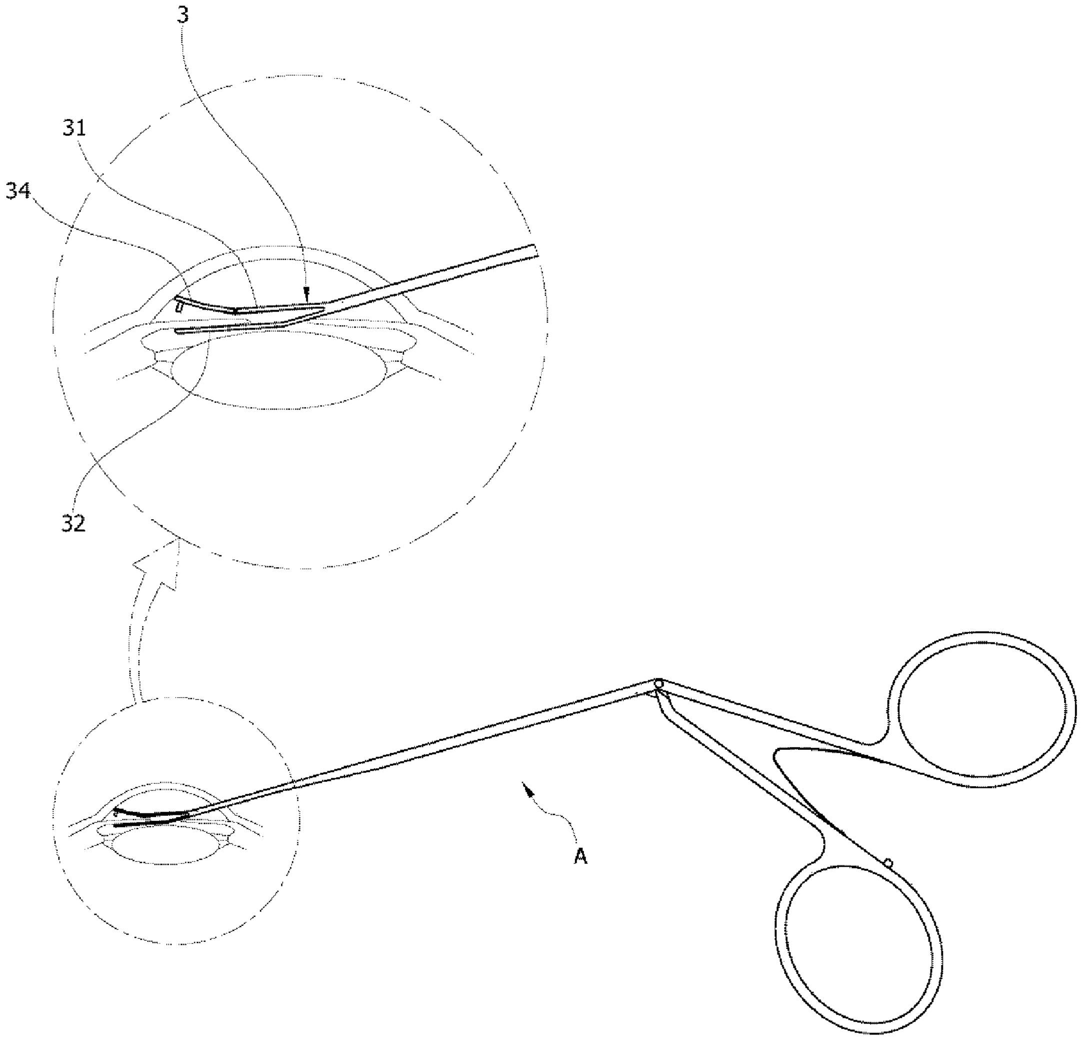

【FIG 7E】
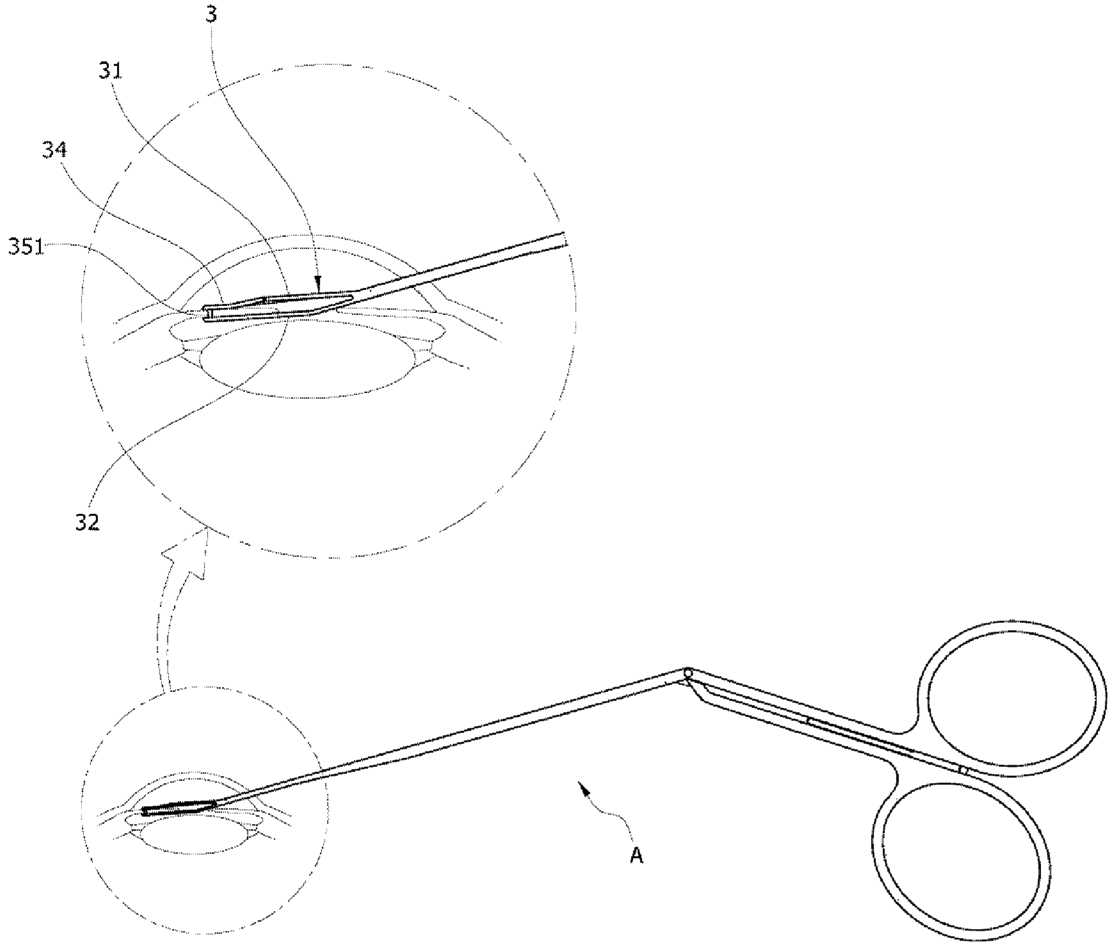

【 FIG 7F】
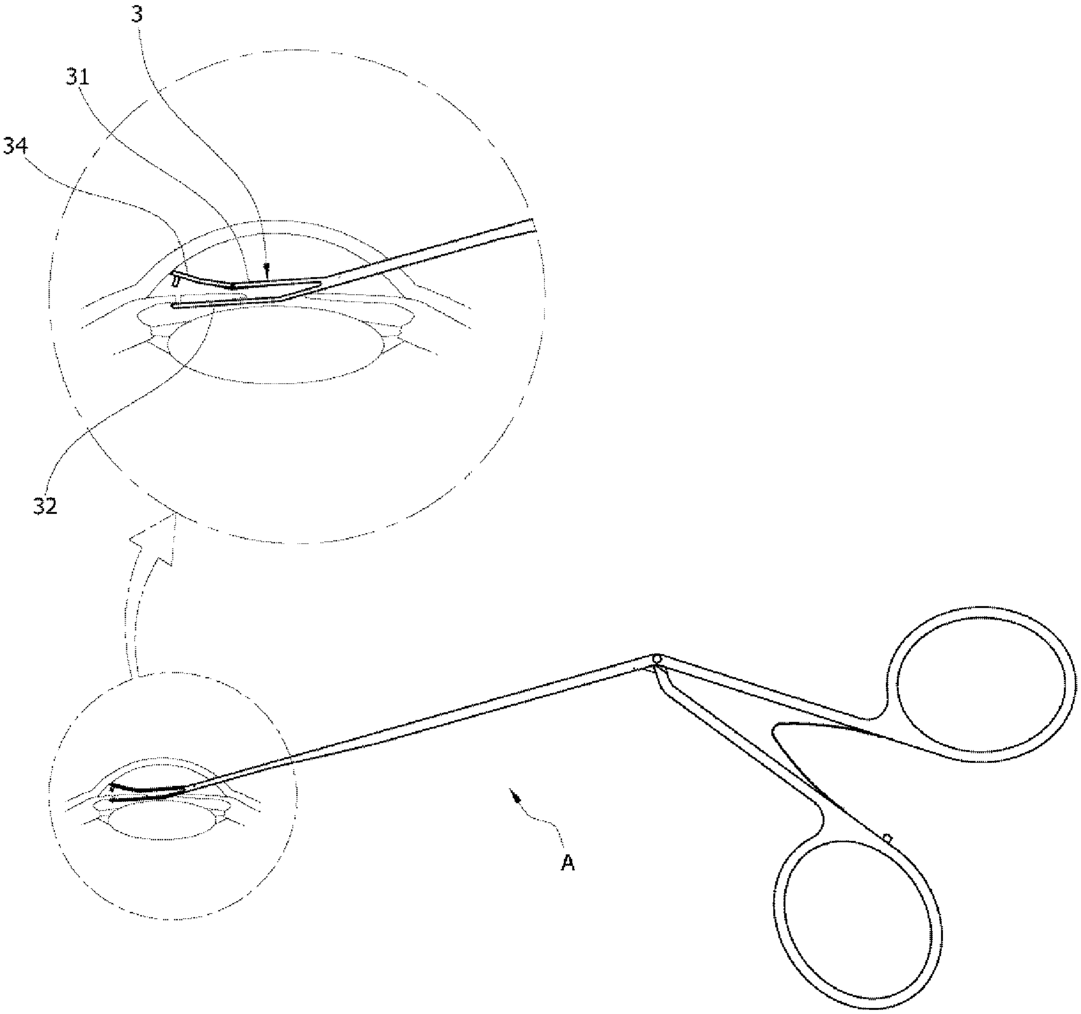

PUNCHING-TYPE IRIDOTOMY INSTRUMENT

CROSS REFERENCE TO RELATED APPLICATIONS

This application is a National Stage of International Application No. PCT/KR2022/006217 filed on Apr. 29, 2022, claiming priority based on Korean Patent Application No. 10-2021-0056618 filed on Apr. 30, 2021, the entire disclosures of which are incorporated herein by reference.

TECHNICAL FIELD

The present invention relates to a punching-type iridotomy instrument, and more particularly, to a punching-type iridotomy instrument which, in iridectomy, increases the size and positioning accuracy iris incision through structural improvement in a perforation method, thereby shortening the surgery time and facilitating the convenience of surgical procedures.

BACKGROUND ART

Glaucoma refers to an ophthalmic disease caused by abnormalities in the optic nerve, which transmits light entering the eye to the brain, resulting in impaired vision and visual field defects. Examples of risk factors for glaucoma include high intraocular pressure, optic nerve disk hemorrhage, nearsightedness, and thin central corneal thickness.

The aforementioned glaucoma may be broadly classified into open-angle glaucoma and closed-angle glaucoma, depending on the mechanism of impairment of aqueous humor drainage. In the case of closed-angle glaucoma, intraocular pressure increases as the iris around the trabeculae blocks the drainage of aqueous humor through the trabeculae. When acute closed-angle glaucoma is caused by an increase in intraocular pressure, the rapid increase in intraocular pressure causes obvious symptoms such as severe eye pain, headaches, and decreased vision. In addition, if glaucoma is not detected and treated early and properly, permanent vision defects are left behind, and severe glaucoma may even cause blindness.

To treat acute closed-angle glaucoma, iridectomy, which is a surgery that reduces intraocular pressure by creating a small hole in the peripheral iris and draining the aqueous humor, may be used.

Corneal transplantation refers to a surgical procedure that removes the recipient's diseased corneal flap and transplants a clear corneal flap from a donor to treat deterioration in vision caused by a cloudy or edematous cornea. Descemet membrane endothelial keratoplasty (DMEK) or Descemet Stripping automated endothelial keratoplasty (DSAEK) is performed to transplant only the problematic endothelial flap while leaving the normal corneal tissue behind. The iris incision for preventing pupillary blockage may also be performed by the iridectomy.

However, the iridectomy has traditionally been performed by removing a portion of the iris through an incision in the cornea or sclera and cutting out a portion of the iris with surgical scissors. However, when surgical scissors are used, it is difficult to control the exact location and size of the iris incision, and the incision may cause iris hemorrhage. This iris hemorrhage significantly increases the likelihood of failure of glaucoma (closed-angle glaucoma) surgery and corneal transplantation.

As a result, there is an acute need to research and develop an iridotomy instrument that can perform iridectomy while accurately adjusting the size and position of the iris incision, prevent iris hemorrhage by performing optimal iris incision, shorten the surgery time, and facilitate the convenience of the surgical procedure.

DISCLOSURE

Technical Problem

The present invention has been made in an effort to solve the above-mentioned various problems, and an object of the present invention is to provide a punching-type iridotomy instrument that follows a basic structure and operation mannerism of scissors and accurately sets the size and position of iris incision by improving a structure for forming a hole in a predetermined site of an iris by using a punching method instead of a unique scissor incision method.

Another object of the present invention is to provide a punching-type iridotomy instrument that may more conveniently perform an operation in accordance with a situation by replacing/changing sizes (diameter) and positions of incision (punching) members in consideration of a size and position of iris incision.

Technical Solution

To achieve the above-mentioned objects, the present invention provides a punching-type iridotomy instrument including: a grip manipulation part configured to be manipulated to be opened or closed by a user while being held by the user's hand; an extension shaft extending from the grip manipulation part; and a punching operating unit extending from the extension shaft and configured to perform an operation of forming a hole in a predetermined site of a peripheral portion of an iris in conjunction with an operation of the grip manipulation part performed by the user's manipulation, in which the grip manipulation part includes: a first round shaft extending from a rear side of the extension shaft and having a first finger grip ring formed at an end of the first round shaft and configured to be fitted with the user's thumb; a second round shaft hingedly coupled to a predetermined position on the extension shaft by a pivot pin and having a second finger grip ring formed at an end of the second round shaft and configured to be fitted with the user's ring finger, the second round shaft being configured to implement a rotational operation related to a motion of the ring finger fitted into the second finger grip ring; a spring disposed between the first and second round shafts and configured to exert elasticity for pushing the second round shaft; and a wire configured to connect the second round shaft and the punching operating unit while passing through the extension shaft and operate the punching operating unit in conjunction with a rotational operation of the second round shaft.

In addition, the punching operating unit may include: upper and lower forks extending from a front side of the extension shaft and divided into two pieces to define a spacing interval for accommodating the iris such that the upper and lower forks are respectively positioned outside the iris and inside the iris; a rotary bar hingedly coupled to a tip of the upper fork by a shaft pin and configured to rotate toward the lower fork about the shaft pin by an operation in conjunction with the wire in accordance with a manipulation of the grip manipulation part; and incision members respectively provided at a tip of the lower fork and a tip of the rotary bar and configured to form a hole in the predetermined site of the iris positioned in the spacing interval in conjunction with a rotation of the rotary bar.

Further, the first round shaft may integrally extend from the extension shaft, the first round shaft may have an inclination angle so that the extension shaft is bent downward when the thumb is directed upward in a state in which the thumb and the ring finger are respectively fitted into the first and second finger grip rings, and the inclination angle may be an acute angle larger than 0° and smaller than a right angle based on a length direction of the extension shaft.

In addition, assembling holes may be respectively formed in a tip portion of the lower fork and a tip portion of the rotary bar so that the incision members are coupled to the assembling holes, and the incision member may include: a punch configured to be fitted into the assembling hole, protruding downward from the rotary bar, and configured to form a hole in the predetermined site of the iris in conjunction with the rotation of the rotary bar; and a socket configured to be fitted into the assembling hole of the lower fork to accommodate a distal end of the punch.

Further, a first extension bar may be provided at the tip of the lower fork and configured to increase a length of the lower fork and adjust a position of the socket while being extended from the tip or retracted to the tip, a second extension bar may be provided at the tip of the rotary bar and configured to increase a length of the rotary bar and adjust a position of the punch while being extended from the tip or retracted to the tip, extension/retraction rods may respectively extend from rear ends of the first and second extension bars, and guide holes may be directed inward from the tip of the lower fork and the tip of the rotary bar to allow the extension/retraction rods to be inserted and coupled into the guide holes and to guide extensions and retractions of the extension/retraction rods.

In addition, the punch and the socket may each have a diameter corresponding to a size of iris incision and each be configured to be replaced and used.

Further, a diameter of the punch and a hole of the socket may each have any one of a circular shape, an elliptical shape, and an angular shape.

Advantageous Effects

As can be clearly seen from the above-mentioned description, according to the punching-type iridotomy instrument of the present invention, a hole may be accurately formed at a desired position of the iris based on the user's manipulation of the grip manipulation part and the operation of the punching operating unit in conjunction with the user's manipulation in the state in which the punching operating unit provided in the form of pincers is positioned at a predetermined site of the iris to be incised. This advantage may shorten the surgery time, prevent iris hemorrhage caused by erroneous incision, and prevent complications caused by the iris hemorrhage.

In addition, the incision size of the iris is changed and the incision position of the iris is adjusted by adjusting the length of the lower fork of the punching operating unit and the length of the rotary bar by changing and using the punches and the sockets that constitute the incision member. Therefore, it is possible to obtain the effect of performing the iridectomy customized for each patient and obtaining the best surgical outcome.

Further, through the achievement of the various effects described above, the present invention is a very useful invention that can contribute significantly to the development and revitalization of the medical technology and medical industry related to the treatment of glaucoma (closed-angle glaucoma) or the advancement of iridectomy to prevent pupillary blockage in the process of corneal transplantation (shortening the surgery time, facilitating the convenient surgery, suppressing the occurrence of postoperative complications, etc.).

DESCRIPTION OF DRAWINGS

FIGS. 1 and 2 are perspective and front views illustrating a relationship between components of a punching-type iridotomy instrument according to the present invention.

FIG. 3 is a main enlarged cross-sectional view illustrating a relationship between components of a punching operating unit of the punching-type iridotomy instrument according to the present invention.

FIG. 4 is a main enlarged cross-sectional view illustrating a coupling relationship of an incision member of the punching-type iridotomy instrument according to the present invention.

FIGS. 5A, 5B, and 5C are exemplified configuration views illustrating embodiments of the incision member of the punching-type iridotomy instrument according to the present invention.

FIG. 6 is a main enlarged cross-sectional view illustrating another relationship between the components of the punching operating unit of the punching-type iridotomy instrument according to the present invention.

FIGS. 7A to 7F are use state views stepwise illustrating an iris incision process using the punching-type iridotomy instrument according to the present invention.

MODES OF THE INVENTION

Hereinafter, exemplary embodiments of the present invention will be described in detail with reference to the accompanying drawings so that those skilled in the art to which the present invention pertains may easily carry out the present invention.

First, in giving reference numerals to constituent elements of the drawings, it should be noted that the same constituent elements will be designated by the same reference numerals, if possible, even though the constituent elements are illustrated in different drawings. In addition, in the description of the present invention, the specific descriptions of publicly known related configurations or functions will be omitted when it is determined that the specific descriptions may obscure the subject matter of the present invention.

Among the attached drawings, FIGS. 1 and 2 are perspective and front views illustrating a relationship between components of a punching-type iridotomy instrument according to the present invention, FIG. 3 is a main enlarged cross-sectional view illustrating a relationship between components of a punching operating unit of the punching-type iridotomy instrument according to the present invention, FIG. 4 is a main enlarged cross-sectional view illustrating a coupling relationship of an incision member of the punching-type iridotomy instrument according to the present invention, and FIGS. 5A, 5B, and 5C are exemplified configuration views illustrating embodiments of the incision member of the punching-type iridotomy instrument according to the present invention.

As illustrated in FIGS. 1 to 3, a punching-type iridotomy instrument A according to the present invention includes a grip manipulation part 1 configured to be manipulated to be opened or closed by a user while being held by the user's hand, an extension shaft 2 extending from the grip manipulation part 1 by a predetermined length, and a punching operating unit 3 further extending from the extension shaft 2 by a predetermined length and configured to perform an operation of forming a hole in a predetermined site of a peripheral portion of an iris in conjunction with an operation of the grip manipulation part 1 performed by the user's manipulation.

The grip manipulation part 1 is a part manipulated by the user to operate the punching operating unit 3 and control the operation of the punching operating unit 3. The grip manipulation part 1 includes a first round shaft 11 extending rearward from the extension shaft 2 by a predetermined length and having a first finger grip ring 111 formed at an end of the first round shaft 11 and configured to be fitted with the user's thumb, a second round shaft 13 hingedly coupled to a predetermined position on the extension shaft 2 by a pivot pin 12 and having a second finger grip ring 131 formed at an end of the second round shaft 13 and configured to be fitted with the user's ring finger, the second round shaft 13 being configured to implement a rotational operation related to a motion of the ring finger fitted into the second finger grip ring 131, a spring 14 disposed between the first and second round shafts 11 and 13 and configured to exert elasticity for pushing the second round shaft 13, and a wire 15 configured to connect the second round shaft 13 and the punching operating unit 3 while passing through the extension shaft 2 and operate the punching operating unit 3 in conjunction with a rotational operation of the second round shaft 11.

The first round shaft 11 integrally extends from the extension shaft 2. In case that the thumb is directed upward in a state in which the thumb and the ring finger are respectively fitted into the first and second finger grip rings 111 and 131, the extension shaft 2 is bent downward and has an inclination angle θ that provides a grip shape suitable to incise an iris of a patient lying on an operating table. The inclination angle θ may be an acute angle larger than 0° and smaller than a right angle (90°) based on a length direction of the extension shaft 2.

The extension shaft 2 is a part that spaces the punching operating unit 3 from the grip manipulation part 1 so that the user's body part (hand), which holds the grip manipulation part 1, does not come into contact with the patient's surgical site (an eyeball or the like). The extension shaft 2 may be provided in the form of a rod having a predetermined length, and a wire hole 21, through which the wire 15 may pass, may be formed in (formed through) the extension shaft 2 in the length direction.

The punching operating unit 3 is a part that performs an incision operation of forming a small hole in the predetermined site of the peripheral portion of the iris in conjunction with the rotational operation of the second round shaft 13 of the grip manipulation part 1. As illustrated in FIGS. 3 and 4, the punching operating unit 3 includes upper and lower forks 31 and fork 32 extending from a front side of the extension shaft 2 by a predetermined length and divided into two pieces to define a spacing interval 30 for accommodating the iris such that the upper and lower forks 31 and 32 are respectively positioned outside the iris (at the upper side based on the drawing) and inside the iris (at the upper side based on the drawing), a rotary bar 34 hingedly coupled to a tip of the upper fork 31 by a shaft pin 33 and configured to be rotated toward the lower fork 32 about the shaft pin 33 by an operation (pulling operation) in conjunction with the wire 15 in accordance with the manipulation of the grip manipulation part 1, and incision members 35 respectively provided at a tip of the lower fork 32 and a tip of the rotary bar 34 and configured to form a hole in a predetermined site of the iris positioned in the spacing interval 30 in conjunction with the rotation of the rotary bar 34.

Assembling holes 321 and 341 are respectively formed in tip portions of the lower fork 32 and the rotary bar 34 so that the incision members 35 are coupled to the assembling holes 321 and 341.

The incision members 35 include a punch 351 configured to be fitted into the assembling hole 321, protruding downward from the rotary bar 34 by a predetermined length, and configured to form the hole in the predetermined site of the iris in conjunction with the rotation of the rotary bar 34, and a socket 352 configured to be fitted into the assembling hole 341 of the lower fork 32 to accommodate a distal end of the punch 351.

In this case, a diameter of the punch 351 and a hole size of the socket 352, which accommodates the distal end of the punch 351, may vary depending on a size of the hole to be formed in the predetermined site of the iris. As illustrated in FIGS. 5A, 5B, and 5C, the punches 351 having different diameters and the sockets 352 having different holes may be changed and used. Further, although not illustrated in the drawings, the diameter of the punch 351 and the hole of the socket 352 may have various shapes such as a circular, elliptical, quadrangular, hexagonal, or octagonal shape.

Meanwhile, FIG. 6 is a main enlarged cross-sectional view illustrating another relationship between the components of the punching operating unit of the punching-type iridotomy instrument according to the present invention. The punching operating unit and the rotary bar may vary in configuration in order to adjust a length of the lower fork 32 of the punching operating unit 3 and a length of the rotary bar 34 to adjust the positions of the incision members 35 for each position of an incision site of the iris on which the iridectomy is to be performed.

To this end, as illustrated in FIG. 6, a first extension bar 32-1 is provided at the tip of the lower fork 32 and configured to increase a length of the lower fork 32 and adjust a position of the socket 352 of the punching operating unit 3 while being extended from the tip or retracted to the tip. A second extension bar 34-1 is provided at the tip of the rotary bar 34 and configured to increase a length of the rotary bar 34 and adjust a position of the punch 351 of the punching operating unit 3 while being extended from the tip or retracted to the tip.

In addition, extension/retraction rods 32-11 and 34-11 respectively extend from rear ends of the first and second extension bars 32-1 and 34-1. Guide holes 321 and 341 are directed inward from the tip of the lower fork 32 and the tip of the rotary bar 34 in order to allow the extension/retraction rods 32-11 and 34-11 to be inserted and coupled into the guide holes 321 and 341 and to guide the extensions and retractions of the extension/retraction rods 32-11 and 34-11.

Non-described reference numeral r indicates at least one guide roll having two opposite ends connected to the second round shaft of the grip manipulation part and the rotary bar of the punching operating unit and configured to assist the operation of the wire provided to penetrate the extension shaft in the length direction.

An operation of the punching-type iridotomy instrument A according to the present invention configured as described above will be specifically described below.

First, FIGS. 7A to 7F are use state views stepwise illustrating an iris incision process using the punching-type iridotomy instrument according to the present invention. As illustrated in the drawings, the punching-type iridotomy instrument A of the present invention may be used for iridectomy performed to prevent pupillary blockage during the cornea transplantation or the treatment of closed-angle glaucoma by reducing intraocular pressure by forming a small hole in a peripheral portion of an iris and draining aqueous humor.

Specifically, as illustrated in FIG. 7A, the punching operating unit 3 is inserted into the cornea (eyeball) through cornea incision in the state in which the rotary bar 34, which is disposed forward of the upper fork 31 of the punching operating unit 3 extending from the front side of the extension shaft 2, is closed as the grip manipulation part 1 of the iridotomy instrument A of the present invention, which is held by the user's hand, is manipulated by the user.

Next, as illustrated in FIG. 7B, the punching operating unit 3 is positioned to an edge of the iris. Thereafter, as illustrated in FIG. 7C, the ring finger fitted into the second finger grip ring 131 of the end of the second round shaft 13 of the grip manipulation part 1 is opened so that the rotary bar 34 is moved away from the lower fork 32 of the punching operating unit 3 by the operation in conjunction with the wire 15 related to the operation of rotating the second round shaft 13. Therefore, in a state in which the iris may enter the spacing interval 30 between the upper fork 31 and the lower fork 32, the punching operating unit 3 enters a predetermined site (position) of the iris to be incised in a state in which the upper fork 31 is positioned outside the iris (at the upper side based on the drawing) and the lower fork 32 is positioned inside the iris (at the lower side based on the drawing), as illustrated in FIG. 7D.

In this state, as illustrated in FIG. 7E, the ring finger is closed, and the rotary bar 34 is rotated toward the lower fork 32 about the shaft pin 33 at the tip of the upper fork 31 by the operation (pulling operation) in conjunction with the wire 15 related to the rotation so that the second round shaft 13 of the second finger grip ring 131, which is fitted with the ring finger, comes into close contact with the first round shaft 11 of the grip manipulation part 1 that is fitted with the thumb. Therefore, a desired site of the peripheral portion of the iris is incised (perforated) by the operation in which the punch 351 of the incision member 35 fitted with the assembling hole 341 of the rotary bar 34 is partially accommodated in the socket 352 of the incision member 35 fitted with the assembling hole 321 of the lower fork 32 while penetrating the iris.

Lastly, after the iris incision is completed as described above, the punching operating unit 3 is moved to a central portion of the cornea in a state in which the ring finger is opened so that the rotary bar 34 is moved away from the lower fork 32, as illustrated in FIG. 7F. Thereafter, the incision of the peripheral portion of the iris is ended by taking out the punching operating unit 3 through the cornea incision in a state in which the ring finger is closed so that the rotary bar 34 is in close contact with the lower fork 32.

As a result, according to the punching-type iridotomy instrument A of the present invention, a hole may be accurately formed at a desired position of the iris based on the user's manipulation of the grip manipulation part 1 and the operation of the punching operating unit 3 in conjunction with the user's manipulation in the state in which the punching operating unit 3 is positioned at a predetermined site of the iris to be incised. This advantage may shorten the surgery time, prevent iris hemorrhage caused by erroneous incision, and prevent complications caused by the iris hemorrhage.

In addition, the incision size of the iris is changed and the incision position of the iris is adjusted by adjusting the length of the lower fork 32 of the punching operating unit 3 and the length of the rotary bar 34 at the tip of the upper fork 31 by changing and using the punches 351 and the sockets 352 that constitute the incision member 35. Therefore, it is possible to obtain the effect of performing the iridectomy customized for each patient and obtaining the best surgical outcome.

The above description is simply given for illustratively describing the technical spirit of the present invention, and those skilled in the art to which the present invention pertains will appreciate that various modifications, changes, and substitutions are possible without departing from the essential characteristic of the present invention. Accordingly, the embodiments disclosed in the present invention and the accompanying drawings are intended not to limit but to describe the technical spirit of the present invention, and the scope of the technical spirit of the present invention is not limited by the embodiments and the accompanying drawings. The protective scope of the present invention should be construed based on the following claims, and all the technical spirit in the equivalent scope thereto should be construed as falling within the scope of the present invention.

The invention claimed is:

1. A punching-type iridotomy instrument comprising:

a grip manipulation part configured to be manipulated to be opened or closed by a user while being held by the user's hand;

an extension shaft extending from the grip manipulation part; and a punching operating unit extending from the extension shaft and configured to perform an operation of forming a hole in a predetermined site of a peripheral portion of an iris in conjunction with an operation of the grip manipulation part performed by the user's manipulation, wherein the grip manipulation part comprises:

a first round shaft extending from a rear side of the extension shaft and having a first finger grip ring formed at an end of the first round shaft and configured to be fitted with the user's thumb;

a second round shaft hingedly coupled to a predetermined position on the extension shaft by a pivot pin and having a second finger grip ring formed at an end of the second round shaft and configured to be fitted with the user's ring finger, the second round shaft being configured to implement a rotational operation related to a motion of the ring finger fitted into the second finger grip ring;

a spring disposed between the first and second round shafts and configured to exert elasticity for pushing the second round shaft; and a wire configured to connect the second round shaft and the punching operating unit while passing through the extension shaft and operate the punching operating unit in conjunction with a rotational operation of the second round shaft, and wherein the punching operating unit comprises:

upper and lower forks extending from a front side of the extension shaft and divided into two pieces to define a spacing interval for accommodating the iris such that the upper and lower forks are respectively positioned outside the iris and inside the iris;

a rotary bar hingedly coupled to a tip of the upper fork by a shaft pin and configured to rotate toward the lower fork about the shaft pin by an operation in conjunction with the wire in accordance with a manipulation of the grip manipulation part; and incision members respectively provided at a tip of the lower fork and a tip of the rotary bar and configured to form a hole in the predetermined site of the iris positioned in the spacing interval in conjunction with a rotation of the rotary bar.

2. The punching-type iridotomy instrument of claim 1, wherein the first round shaft integrally extends from the extension shaft, wherein the first round shaft has an inclination angle so that the extension shaft is bent downward when the thumb is directed upward in a state in which the thumb and the ring finger are respectively fitted into the first and second finger grip rings, and wherein the inclination angle is an acute angle larger than 0° and smaller than a right angle based on a length direction of the extension shaft.

3. The punching-type iridotomy instrument of claim 1, wherein assembling holes are respectively formed in a tip portion of the lower fork and a tip portion of the rotary bar so that the incision members are coupled to the assembling holes, and wherein the incision member comprises:

a punch configured to be fitted into the assembling hole, protruding downward from the rotary bar, and configured to form a hole in the predetermined site of the iris in conjunction with the rotation of the rotary bar; and a socket configured to be fitted into the assembling hole of the lower fork to accommodate a distal end of the punch.

4. The punching-type iridotomy instrument of claim 3, wherein the punch and the socket each have a diameter corresponding to a size of iris incision and are each configured to be replaced and used.

5. The punching-type iridotomy instrument of claim 3, wherein a diameter of the punch and a hole of the socket each have any one of a circular shape, an elliptical shape, and an angular shape.

6. The punching-type iridotomy instrument of claim 1, wherein a first extension bar is provided at the tip of the lower fork and configured to increase a length of the lower fork and adjust a position of the socket while being extended from the tip or retracted to the tip, wherein a second extension bar is provided at the tip of the rotary bar and configured to increase a length of the rotary bar and adjust a position of the punch while being extended from the tip or retracted to the tip, wherein extension/retraction rods respectively extend from rear ends of the first and second extension bars, and wherein guide holes are directed inward from the tip of the lower fork and the tip of the rotary bar to allow the extension/retraction rods to be inserted and coupled into the guide holes and to guide extensions and retractions of the extension/retraction rods.

* * * * *